United States Patent
Holgersson et al.

(10) Patent No.: US 6,943,239 B2
(45) Date of Patent: Sep. 13, 2005

(54) ANTIGENIC FUSIONPROTEIN CARRYING GALα1,3GAL EPITOPES

(75) Inventors: Jan Holgersson, Huddinge (SE); Jining Liu, Huddinge (SE)

(73) Assignee: Absorber AB, Stockholm (SE)

( * ) Notice: Subject to any disclaimer, the term of this patent is extended or adjusted under 35 U.S.C. 154(b) by 0 days.

(21) Appl. No.: 09/194,396

(22) PCT Filed: Mar. 26, 1998

(86) PCT No.: PCT/SE98/00555

§ 371 (c)(1),
(2), (4) Date: Dec. 8, 1998

(87) PCT Pub. No.: WO98/42750

PCT Pub. Date: Oct. 1, 1998

(65) Prior Publication Data

US 2002/0028205 A1 Mar. 7, 2002

(30) Foreign Application Priority Data

Mar. 26, 1997 (SE) .............................................. 9701127

(51) Int. Cl.⁷ ................................................. C07K 1/00
(52) U.S. Cl. ...................... 530/402; 530/300; 530/403; 530/415; 530/387.3
(58) Field of Search ........................ 424/178.1, 192.1, 424/193.1; 530/387.3

(56) References Cited

U.S. PATENT DOCUMENTS 5,434,131 A * 7/1995 Linsley et al.

FOREIGN PATENT DOCUMENTS

| WO | WO 94/10309 | 5/1994 |
| WO | WO 94/21799 | 9/1994 |
| WO | WO 97/07823 | 3/1997 |

OTHER PUBLICATIONS

Sako, et al. 1993 Cell 1751 1179–1186, 1993.*
Tsuni, et al 1990 Chem. Pharm. Bulletin (38) 765–768, 1990.*
Godink, 1983 Monoclonal Abs :Principles & Practice p. 117, Table 4.2, 1983.*
Kozlowski et al. Transplantation Proceedings, p. 961, 1997.*
R. Rieben et al., "Detection, Immunoabsorption, and Inhibition of Cytotoxic Activity of Anti–alpha–Gal Antibodies Using Newly Developed Substances with Synthetic Gal alpha–1–3Gal Disaccharide Epitopes", Dialog Information Services, file 5:Biosis Previews (R), Xenotransplantation 2 (2), 1995.
Mauro S. Sandrin et al., "Natural Human Anti–Galα(1,3) Gal Antibodies React with Human Mucin Peptides", Glycoconjugate Journal (1997) 14:97–105, pp. 97–104.

* cited by examiner

Primary Examiner—G. R. Ewoldt
(74) Attorney, Agent, or Firm—Mintz, Levin, Cohn, Ferris, Glovsky and Popeo, P.C.; Ivor R. Elrifi; Cynthia A. Kozakiewicz (57) ABSTRACT

The present invention relates to an antigenic fusionprotein, which carries multiple Galα1,3Gal epitopes. The fusion protein according to the invention may also be comprised of a heavily glycosylated mucin part, which mediates binding to selectins, such as PSGL-1, and a part, which exhibits immunoglobulin properties, such as the Fc part of IgG. The fusionprotein according to the invention is preferably used as an absorber to prevent a hyperacute rejection of a xenotransplant, such as a pig tissue or organ transplanted into a human patient. In addition, the invention relates to a method for the prevention of hyperacute rejection reaction in a patient who is to receive a xenotransplant.

3 Claims, 6 Drawing Sheets

ANTIGENIC FUSIONPROTEIN CARRYING GALα1,3GAL EPITOPES

TECHNICAL FIELD

The present invention relates to antigenic fusionproteins carrying multiple Galα1,3Gal-epitopes for the removal of foreign antibodies, such as xenoreactive human anti-pig antibodies, by absorption.

BACKGROUND

Many diseases are today curable only by a transplantation of tissue or an organ, such as a kidney or heart. It is sometimes possible to locate a living donor with immunological markers compatible with the transplant recipient, although organ donation by a living donor involves great risks and possible deleterious health effects for the donor. Without any available living donor, the organ must be obtained from a heartbeating human cadaver of high quality and, again, there must be a good immunological match between the donor and the recipient. The situation today is a steadily increasing demand for human organs suitable for transplantation and the gap between said demand and the availability of organs is likely to grow even wider in view of the continuing improvements made in transplantation procedures and outcome. The most promising possible answer to this problem is xenotransplantation, i.e. transplantation of tissue or organs between different species. For human patients, the pig is considered the most suitable donor species for medical, practical, ethical and economical reasons.

The main problem in xenografting between discordant species, such as pig to human, is the hyperacute rejection (HAR), which leads to a cessation of the blood flow within minutes following a transplantation. Even though other mechanisms of rejection will ensue after HAR, the general belief is that if HAR could be prevented, the patient's immune system may undergo a process of accommodation, whereafter a conventional immunosuppressive regimen could maintain the compatibility of the patient and the xenograft.

The HAR is caused by preformed, natural antibodies in the receiving species reacting with antigens on the endothelium in donor organs, an interaction which leads to complement and endothelial cell activation, thrombosis, extravasation of white blood cells and, eventually, rejection. Pig antigens reacting with human, natural antibodies have turned out to be carbohydrates (7–10); the major one being the Galα1,3Gal epitope which is not expressed in old world monkeys, apes and humans due to an inactivation of the α1,3 galactosyltransferase (GT) (10–12).

Several methods have been proposed for the removal or elimination of xenoreactive antibodies from the blood of a recipient. Bach et al (*Xenotransplantation*, Eds: Cooper, D. K. C., et al, Springer Verlag, 1991, Chapter 6) proposed the perfusion of the recipients blood through an organ of the proposed donor species prior to transplantation of another, fresh organ, whereby anti-pig antibodies were removed.

Plasmapheresis has also been proposed for a non-specific removal of naturally occurring antibodies, whereby the graft survival is prolonged (e.g. Cairns et al, Rydberg et al). However, conventional plasmapheresis, or plasma exchange, results in loss of blood volume, which in turn may require a volume replacement with pooled preparations of fresh frozen plasma, human albumin, immunoglobulin etc. In addition, coagulation factors, platelets and antithrombotic factors must also be replaced. Such a treatment carries not only the risk of virus transfer, such as HIV, but also the risk of an anaphylactic reaction to foreign substances. Other negative side effects of plasmapheresis are recipient sensitization and activation of the complement and clotting system. Accordingly, plasmapheresis does not appear to be either practical or safe.

Other methods for the removal of xenoreactive antibodies involve non-specific antibody removal. Protein A, a major component of the cell wall of *S. aureus*, has a high affinity for a portion of the Fc-region of sub-classes 1, 2 and 4 of immunoglobulin G (IgG1, IgG2, IgG4) and has been used for the non-specific removal of anti-HLA antibodies from hypersensitized patients in need of kidney transplants. The efficacy of the Protein A column treatment after kidney transplantation have been reported (Dantal J., et al, *New England J. Med.* 550: 7–14, 1994; Nilsson, I. M. et al, *Blood* 58: 38–44, 1981; Palmer, A., et al., *The Lancet* Jan. 7, 1989, pp. 10–12). One essential drawback with the use of a Protein A column technique in the context of xenotransplantation is, however, the fact that only IgG will be removed. Lately, it has been shown that the antibodies involved in HAR during a transplantation from pig to human may involve several other immunoglobulin classes. In addition, the non-specific antibody removal will cause a general deterioration of the patients immune defense, which quite naturally is not desirable during such a process as a transplantation procedure, where the patient is immunosuppressed.

Leventhal et al (WO 95/31209) propose a method of preventing or ameliorating a hyperacute reaction occurring after transplantation of a pig organ to a primate recipient, including a human. The method involves passing the recipients plasma over a column with a coupled protein, which binds to and thereby removes immunoglobulin therefrom. The protein is selected from a group consisting of *Staphylococcus aureus* protein A, *Streptococcus* protein G and anti-human immunoglobulin antibodies. This method suffers from the same drawbacks as depicted above for the protein A column.

It has been shown (Platt et al, Good et al, Holgersson et al) that pig antigens reacting with human, natural antibodies are carbohydrates, the major one being the Galα1,3Gal epitope, which is not expressed in old world monkeys, apes and humans due to an inactivation of the α1,3 galactosyltransferase.

Recently, McKenzie et al showed that COS cells transfected with the α1,3-galactosyltransferase cDNA expressed the Galα1,3Gal-epitope on their surfaces and could absorb most of the human anti-pig activity from human serum.

Further, Galα1,3Gal-derivatized columns have been used to specifically remove anti-pig activity from human serum (22), free Galα1,3Gal disaccharides have been shown to prevent binding of anti-pig antibodies to porcine cells, including endothelium (23), and so has porcine stomach mucin (24). However, organic synthesis of saccharides is a very laborious and expensive method, which in addition is rather slow, and accordingly, has not found any wide spread applicability.

Apart from the HAR, xenografts are still typically rejected within days in a process that has been termed delayed xenograft rejection (DXR) (29). DXR is characterized by mononuclear cell activation and graft infiltration, as well as cytokine production (29). The importance of the Galα1,3Gal epitope for these cellular events is not known, although human anti-Galα1,3Gal antibodies were recently shown to be involved in antibody-dependent cellular cytotoxicity (ADCC) of porcine cells (30).

Thus, there is still a need of cheaper and more efficient methods for the elimination of foreign antibodies, such as pig-antibodies, from the blood from a recipient who is to obtain a xenotransplant. In addition, within the field of xenotransplantation, of methods for the prevention of DXR.

SUMMARY OF THE INVENTION

The objective of the present invention is to fulfill the above defined need. Accordingly, the present invention provides an antigenic fusionprotein, which carries multiple Galα1,3Gal epitopes. In a preferred embodiment, the fusionprotein according to the present invention is comprised of a heavily glycosylated mucin part, which may mediate binding to the selectins, and a part conferring immunoglobulin properties. The fusionprotein according to the invention carries a multitude of Galα1,3Gal epitopes, that effectively absorbs foreign antibodies, such as anti-pig antibodies, involved in antibody-dependent, complement-mediated killing and ADCC of endothelial cells, such as porcine cells.

DETAILED DESCRIPTION OF THE INVENTION

The present invention relates to an antigenic fusionprotein, which carries multiple Galα1,3Gal epitopes.

Thus, the antigenic fusionprotein according to the present invention is capable of binding preformed antibodies as well as antibodies produced as a response to a transplanted tissue or organ originating from the species in which the Galα1, 3epitopes are expressed, said species preferably being a species different from the antibody producing species. In a preferred embodiment, the antibody producing species is a human being producing antibodies against a foreign transplant, e.g. a pig organ, in which case the Galα1,3 epitopes are synthesized by a α1,3 galactosyltransferase of pig origin. The transplant may be an organ such as a liver, a kidney, a heart etc., or tissue thereof. Accordingly, in the most preferred embodiment of the fusionprotein according to the invention, the antigenic fusionprotein carries multiple Galα1,3Gal epitopes synthesized by a α1,3 galactosyltransferase derived from a porcine species.

Thus, as the fusionprotein according to the present invention may be prepared by the culture of genetically manipulated cells, such as COS cells, it is both cheaper and easier to produce than the previously saccharides produced by organic synthesis. Even though a COS cell expressing the Galα1,3Gal epitope on its surface has been described (12), the present invention is the first proposal of a recombinant fusionprotein, which carries multiple such epitopes. The fusionprotein according to the invention can easily be designed to include other peptides and parts, which may be advantageous for a particular application. Examples of other components of the fusionprotein according to the invention will be described more detailed below.

Thus, in a preferred embodiment, the antigenic fusionprotein according to the invention further comprises a part, which mediates binding to selectin, such as P-selectin. Said part is preferably a highly glycosylated protein, such as a protein of mucin type. The mucins are due to their high content of O-linked carbohydrates especially advantageous together with the Galα1,3Gal epitope in the fusionprotein according to the invention, as the antigenic properties in the present context thereby are greatly improved. Thus, it has been shown that the binding of antibodies which are reactive with the Galα1,3Gal epitope is even more efficient if said epitope is presented by a protein of mucin type, which indicates that the binding in fact may involve more than said epitope alone.

In the hitherto most preferred embodiment of the fusionprotein according to the invention, the part that mediates binding to selectin is the P-selectin glycoprotein ligand-1 (PSGL-1) or an essential part thereof. However, other cell membrane-anchored proteins containing mucin-type domains have been characterized and may be used in the fusionprotein according to the invention as appropriate, such as CD34, CD43, GlyCAM-1, PSGL-1, MAdCAM, CD96, CD45 and RBC glycophorins. In the experimental part of the present application, an example wherein said P-selectin glycoprotein ligand-1 (PSGL-1) is derived from HL-60 cells, is shown. Theoretically, the anti-pig antibody repertoire may recognize the Galα1,3Gal epitope in various structural contexts determined by the core saccharide presenting the epitope, neighbouring branching points, and the proximity to other sugar residues such as fucose and sialic acid (31–33). If Galα1,3Gal disaccharides or Galα1,3Galβ1, 4GlcNAc trisaccharides are used as absorbers some specificities of the repertoire might not be efficiently absorbed.

The properties of the part of the fusionprotein mediating selectin binding according to the invention as well as further reasoning concerning the choice thereof is further discussed below, see the section "Discussion".

In an especially advantageous embodiment, the antigenic fusionprotein according the present invention further comprises a part which confers immunoglobulin properties. The immunoglobulin parts are advantageous for the design of an efficient and simple method of coupling the fusionprotein according to the invention to a solid support to be used for purifying plasma from a recipient of a xenotransplant from antibodies against said transplant. An immunoglobulin part can also be included in the fusion protein according to the invention in the preferred case, where the fusionprotein is produced in a cell which secretes it, whereafter the immunoglobulin part is used for the purification of said secreted fusionprotein from the culture.

Thus, according to an advantageous embodiment of the antigenic fusionprotein according to the present invention, the part that confers immunoglobulin properties is an immunoglobulin or a part thereof, such as IgG or a part thereof. Preferably, said part that confers immunoglobulin properties is the Fc part of an immunoglobulin, preferably of IgG, or an essential part thereof. In a particular embodiment of the present invention, said immunoglobulin property conferring part is $IgG_{2b}$, preferably the Fc part thereof. In an example of a fusionprotein according to the present invention, said part that confers immunoglobulin properties is of nonhuman origin, and is preferably derived from mouse. However, for certain applications said part might more preferably be of human origin.

The fusionprotein according to the present invention is preferably a recombinant fusionprotein. It may have been produced in a recombinant cell line, preferably an eukaryotic cell line, e.g. a COS cell line, following cotransfection of the cDNA for the mucin/immunoglobulin fusion protein and the cDNA for the porcine α1,3 galactosyltransferase.

The fusionprotein according to the present invention may for example be used as an absorber for elimination of antibodies from blood plasma. The use is dicussed in more detail below, in the section "Discussion".

Another aspect of the present invention is cDNA molecule, which comprises a cDNA sequence coding for a fusionprotein as defined above or a derivative or variant thereof.

Yet another aspect of the present invention is a vector, which comprises the cDNA molecule as described above together with appropriate control sequences, such as primers etc. The skilled in the art can easily choose appropriate elements for this end.

Another aspect of the present invention is a cell line transfected with the above defined vector. The cell line is preferably eukaryotic, e.g. a COS cell line. In the preferred embodiment said cells are secreting the fusionprotein according to the invention into the culture medium, which makes the recovery thereof easier and, accordingly, cheaper than corresponding methods for synthesis thereof would be.

Another aspect of the invention is an absorber comprised of a fusionprotein according to the present invention coupled to a solid support. The absorber according to the invention is used in a pretransplant extracorporeal immunoabsorption set up to remove anti-pig antibodies involved in antibody dependent, complement- as well as cell-mediated cytotoxicity of pig endothelial cells.

Finally, a last aspect of the invention is a method of purifying blood plasma from foreign antibodies, e.g. elimination of anti-pig antibodies from human blood plasma. The method involves withdrawal of plasma from a patient, such as a patient who is to receive a transplant of porcine origin, bringing said plasma in contact with a fusionprotein according to the invention to bind anti-pig antibodies thereto, whereby the anti-pig antibodies are eliminated from the plasma, and thereafter reinfusing the plasma into the patient. The method according to the invention has been shown to be more efficient than the previously known methods in the prevention of HAR, possibly thanks to the large amount of carbohydrate in the fusionprotein. Indeed, it is feasable that the present method also contributes in a prevention of delayed xenograft rejection (DXR), as the spectra of antibodies eliminated by the fusionprotein according to the invention presumably is broader than in the prior methods.

EXPERIMENTAL

In the present application, the following abbrevations are used: ADCC, antibody-dependent cellular cytotoxicity; BSA, bovine serum albumin; DXR, delayed xenorejection; ELISA, enzyme-linked immunosorbent assay; FT, fucosyltransferase; Gal, D-galactose; GT, galactosyltransferase; Glc, D-glucose; GlcNAc, D-N-acetylglucosamine; GlyCAM-1, glycosylation-dependent cell adhesion molecule-1; HAR, hyperacute rejection; Ig, immunoglobulin; MAdCAM, mucosal addressin cell adhesion molecule; PAEC, porcine aortic endothelial cells; PBMC, peripheral blood mononuclear cells; PSGL-1, P-selectin glycoprotein ligand-1; RBC, red blood cell; SDS-PAGE, sodium dodecyl sulphate-polyacrylamide gel electrophoresis Materials and Methods Cell culture. COS-7 m6 cells (35) and the SV40 Large T antigen immortalized porcine aortic endothelial cell line, PEC-A (36), were passaged in Dulbecco's modified Eagle's medium (DMEM), with 10% fetal bovine serum (FBS) and 25 µg/ml gentamicin sulfate. The human erythroleukemic cell line, K562, and the Burkitt's lymphoma cell line, Raji, were obtained from ATCC and cultured in HEPES-buffered RPMI 1640 with 10% FBS, 100 IU/ml penicillin and 100 µg/ml streptomycin.

Construction of expression vectors. The porcine α1,3 GT (37–39) was PCR amplified off pig spleen cDNA using a forward primer having six codons of complementarity to the 5' end of the coding sequence, a Kozak translational initiation concensus sequence and a Hind3 restriction site, and a reverse primer with six codons of complementarity to the 3' end of the coding sequence, a translational stop and a Not1 restriction site. The amplified α1,3GT cDNA was cloned into the polylinker of CDM8 using Hind3 and Not1 (35). The P-selectin glycoprotein ligand-1 (PSGL-1)—a highly glycosylated mucin-type protein mediating binding to P-selectin (40)—coding sequence was obtained by PCR off an HL-60 cDNA library, cloned into CDM8 with Hind3 and Not1, and confirmed by DNA sequencing. The mucin/immunoglobulin expression plasmid was constructed by fusing the PCR-amplified cDNA of the extracellular part of PSGL-1 in frame via a BamH1 site, to the Fc part (hinge, CH2 and CH3) of mouse $IgG_{2b}$, carried as an expression casette in CDM7 (Seed, B. et al, unpublished).

Production and purification of secreted mucin/immunoglobulin chimeras. COS m6 cell were transfected using the DEAE-dextran protocol and 1 µg of CsCl-gradient purified plasmid DNA per ml transfection cocktail. COS cells were transfected at approximately 70% confluency with empty vector (CDM8), the $PSGL1/mIgG_{2b}$ plasmid alone or in combination with the α1,3GT encoding plasmid. Transfected cells were trypsinized and transferred to new flasks the day after transfection. Following adherence for approximately 12 hrs, the medium was discarded, the cells washed with phosphate buffered saline (PBS), and subsequently incubated another 7 days in serum-free, AIM-V medium (cat.nr. 12030, Life technologies Inc.). After incubation, supernatants were collected, debris spun down (1400xg, 20 minutes), and $NaN_3$ added to 0.02%. PSGL1/$mIgG_{2b}$ fusion protein was purified on goat anti-mouse IgG agarose beads (A-6531, Sigma) by rolling head over tail, over night at 4° C. The beads were washed in PBS and subsequently used for SDS-PAGE and Western blot analysis, or for absorption of human AB serum and purified human immunoglobulins.

Purification of human IgG, IgM and IgA. Human IgG, IgM and IgA were purified from human AB serum—pooled from more than 20 healthy blood donors—using goat anti-human IgG (Fc specific; A-3316, Sigma), IgM (µ-chain specific; A-9935, Sigma), and IgA (α-chain specific; A-2691, Sigma) agarose beads. Briefly, 5 ml of slurry (2.5 ml packed beads) were poured into a column of 10 mm diameter and washed with PBS. Ten milliter of human pooled AB serum was applied at 1 ml/minute using a peristaltic pump, washed with several column volumns of PBS, and eluted with 0.1 M glycine, 0.15 M NaCl, pH 2.4 using a flow rate of 1 ml/minute. One milliliter fractions were collected in tubes containing 0.7 ml of neutralizing buffer (0.2 M Tris/HCl, pH 9). The absorption at 280 nm was read spectrophotometrically and tubes containing protein were pooled. dialyzed against 1% PBS, and lyophilized. Lyophilized immunoglobulins were resuspended in distilled water and the concentrations adjusted to 16 mg/ml for IgG, 4 mg/ml for IgA and 2 mg/ml for IgM.

SDS-PAGE and Western blotting. SDS-PAGE was run by the method of Leammli with a 5% stacking gel and a 6 or 10% resolving gel using a vertical Mini-PROTEAN II electrophoresis system (Bio-Rad, Herculus, Calif.) (41). Separated proteins were electrophoretically blotted onto Hybond™-C extra membranes (Amersham) using a Mini Trans-Blot electrophoretic transfer cell (Bio-Rad, Herculus, Calif.) (42). Protein gels were stained using a silver staining kit according to the manufacturer's instructions (Bio-Rad, Herculus, Calif.). Following blocking for at least 2 hrs in 3% BSA in PBS, the membranes were probed for 2 hrs in room temperature with peroxidase-conjugated *Bandereia simplicifolia* isolectin $B_4$ (L-5391, Sigma) diluted to a concentration of 1 µg/ml in PBS, pH 6.8 containing 0.2 mM $CaCl_2$. The membranes were washed 5 times with PBS, pH 6.8, and bound lectin was visualized by chemiluminescens using the ECL™ kit according to the instructions of the manufacturer (Amersham).

Quantification of PSGLb1/mIgG$_{2b}$ by anti-mouse IgG Fc ELISA. The concentration of fusion protein in cell culture supernatants before and after absorption was determined by a 96-well ELISA assay, in which fusion proteins were captured with an affinity purified, polyclonal goat anti-mouse IgG Fc antibody (cat.nr. 55482, Cappel/Organon Teknika, Durham, N.C.). Following blocking with 3% BSA in PBS, the fusion proteins were captured and detected with a peroxidase-conjugated, affinity purified, polyclonal anti-mouse IgG Fc antibody (cat.nr. 55566, Organon Teknika, Durham, N.C.) using O-phenylenediamine dihydrochloride as substrate (Sigma). The plate was read at 492 nm and the ELISA calibrated using a dilution series of purified mouse IgG Fc fragments (cat.nr. 015-000-008, Jackson ImmunoResearch Labs., Inc., West Grove, Pa.) resuspended in AIM V serum-free medium.

Porcine aortic endothelial cell ELISA. PEC-A cells were seeded at a density of 15000 cells/well in gelatin-coated 96-well plates (Nunclon, Denmark) and cultured for 48 hrs in AIM V serum-free medium. The plate was washed 5 times in 0.15M NaCl containing 0.02% Tween 20 and incubated for 1 hr in room temperature with 50 µl/well of purified human IgG, IgM, and IgA in PBS, starting at a concentration of 8, 1, and 2 mg/ml, respectively. The plate was washed again as above, and 50 µl of alkaline phosphatase-conjugated goat anti-human IgG (γ-chain specific; A3312, Sigma), IgM (µ-chain specific; A1067, Sigma) and IgA (α-chain specific; A3062, Sigma) F(ab)'$_2$ fragments diluted, 1:200 in PBS were added and incubated for 1 hr at room temperature. The plate was washed as above, incubated with the substrate p-nitrophenyl phosphate (Sigma 104–105), and read at 405 nm.

Porcine aortic endothelial cell cytotoxicity assay. PEC-A cells were seeded and cultured in 96-well plates as described for the PEC-A ELISA. Following 48 hrs of culture, the cells were loaded for 1 hr at 37° C. with Na$_2$$^{51}$CrO$_4$ (cat.nr. CJS4, Amersham), 1 µCi/well, and washed 3 times with AIM V medium. Fifty microliter of serially diluted, absorbed or non-absorbed human AB serum or purified human IgG, IgA, or IgM antibodies were added together with 50 µl of rabbit serum (Cat. no. 439665, Biotest AG, Dreieich, Germany) as a source of complement. Following 4 hrs incubation at 37° C. in a 5% CO$_2$ atmosphere, the supernatants were harvested using a Skatron supernatant collection system (Skatro Instruments, Norway) and analyzed in a γ-counter (1282 Compugamma, LKB Wallac). Each serum and Ig sample were analyzed in triplicate. The percent killing was calculated as the measured minus the spontaneous release divided by the difference between the maximum and the spontaneous release.

Antibody-dependent cellular cytotoxicity (ADCC). Human PBMC were isolated from fresh buffy coats prepared from healthy donors at the Blood bank of the South hospital, Stockholm. Six milliliter of buffy coat was mixed in a 50 ml polypropylene tube with 15 ml of PBS containing 1 mg/ml BSA and 3.35 mg/ml EDTA. Following centrifugation at 500×g for 10 minutes, the platelet rich supernatant was discarded, and 6 ml of the lower phase was mixed with 6 ml of Hank's balanced salt solution (HBSS), and underlayered with 6 ml of Lymphoprep™ (Nycomed Pharma AS). Following centrifugation (800×g, 20 min.), the interface was transferred to a new tube, washed three times in HBSS, and resuspended in serum-free AIM V medium. The final step in the effector cell preparation was to transfer the PBMC to tissue culture flasks that were incubated for 1 hr at 37° C. and 5% CO$_2$ to remove plastic-adherent cells. Target cells were K562 and Raji cells kept as described above, or PEC-A cells that had been trypsinized the day before the assay and subsequently cultured in AIM V serum-free medium to prevent readhesion to the plastic surface. At the time for the assay the PEC-A cells were washed off the bottom of the flask. Target cells were loaded with Na$_2$$^{51}$CrO$_4$, 100 µCi/1× 10$^6$ cells, for 1 hr at 37° C., washed 3 times in HBSS and resuspended in AIM V to a final concentration of 5×10$^4$/ml. Five thousand target cells were added to each well with effector cells in 200 µl AIM V medium with and without 10% heat-inactivated, human AB serum at an effector (E):target (T) ratio ranging from 50:1 in two-fold dilutions to 6.25:1.

Spontaneous release was read in wells with 5 000 target cells incubated in 200 µl AIM V medium without effector cells and maximum release was read in wells where 5 000 target cells in 100 µl AIM V were incubated with 100 µl 5% Triton X-100. Each E:T ratio was analyzed in triplicate. Following incubation at 37° C. for 4 hrs, the supernatants were harvested using a Skatron supernatant collection system (Skatro Instruments, Norway) and analyzed in a γ-counter (LKB Wallac). The percent killing was calculated as the measured minus the spontaneous release divided by the difference between the maximum and the spontaneous release.

Results

Figure 1:
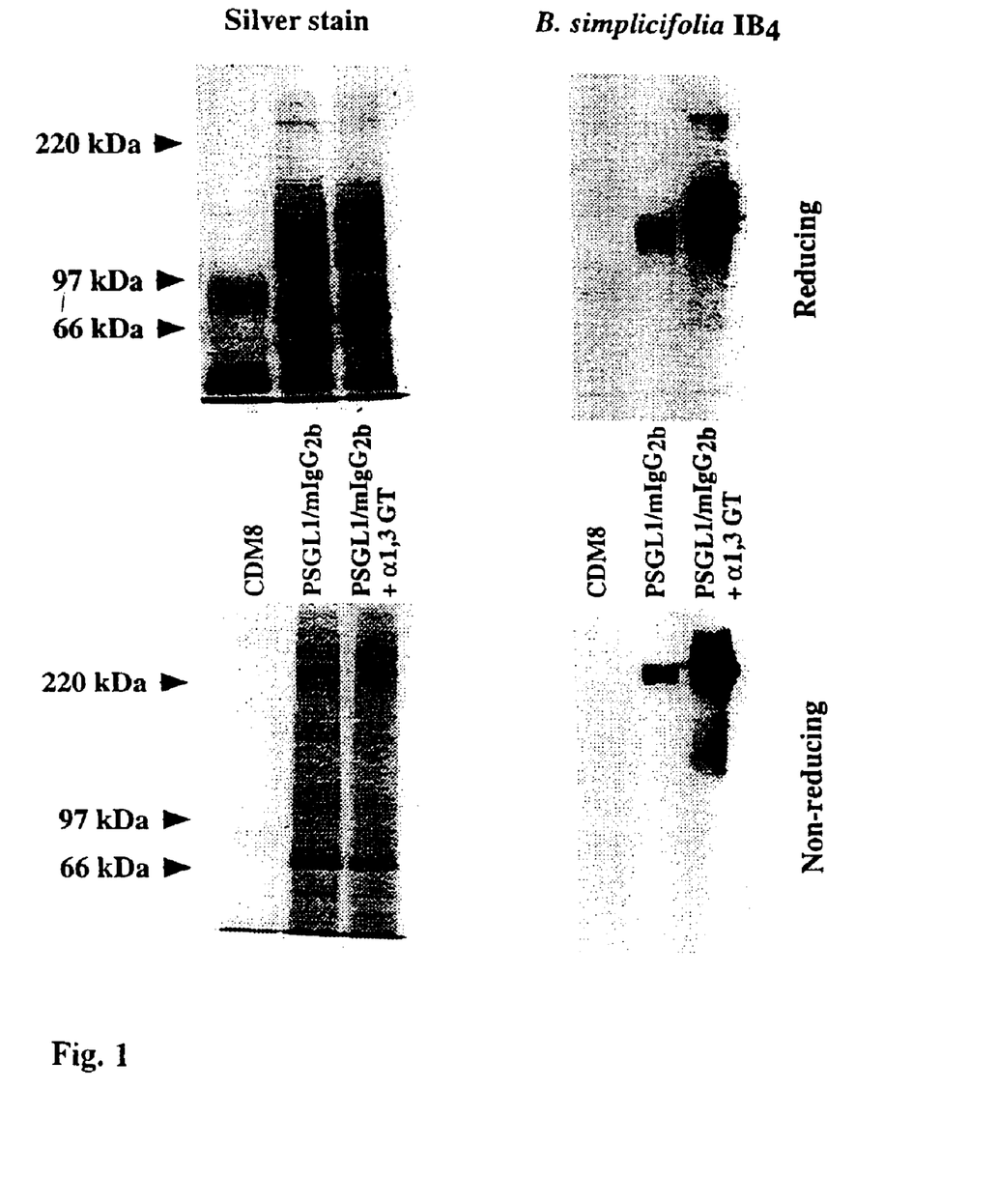

Expression and characterization of the PSGL1/mIgG$_{2b}$ fusion protein. Supernatants from COS-7 m6 cells transfected with the vector plasmid CDM8, the PSGL1/mIgG$_{2b}$ plasmid, or the, PSGL1/mIgG$_{2b}$ together with the porcine α1,3 GT plasmid, were collected approximately 7 days after transfection. Secreted mucin/Ig fusion proteins were purified by absorption on anti-mouse IgG agarose beads and subjected to SDS-PAGE and Western blotting using the *Bandereia simplicifolia* isolectin B$_4$ (BSA IB$_4$) for detection. As seen in FIG. 1, the fusion protein migrated under reducing conditions as a broad band with an apparent molecular weight of 145 kDa that stained relatively poorly with silver. The heterogeneity in size, approximately 125 to 165 kDa, and poor stainability is in concordance with previous observations with respect to the behavior of highly glycosylated, mucin-type proteins (43, 44). The fusion protein is most likely produced as a homodimer because SDS-PAGE under non-reducing conditions revealed a double-band of an apparent molecular weight of more than 250 kDa. The amounts of fusion protein affinity-purified from the two supernatants derived from the same number of COS cells transfected with the PSGL1/mIgG$_{2b}$ plasmid alone or together with the α1,3GT plasmid, respectively, were similar. Probing the electroblotted membranes with BSA IB$_4$ revealed strong staining of the fusion protein obtained following cotransfection with the porcine α1,3 GT (FIG. 1). It is clear, though, that the PSGL1/mIgG$_{2b}$ fusion protein produced in COS-7 m6 cells without cotransfection of the α1,3 GT CDNA also exhibited weak staining with the BSA IB$_4$ lectin, in spite of the fact that COS cells are derived from the Simian monkey—an old world monkey lacking α1,3 GT activity. This indicates that the BSA IB$_4$ lectin has a slightly broader specificity than just Galα1,3Gal epitopes (45). Nevertheless, cotransfection of the porcine α1,3GT cDNA supported the expression of a highly Galα1,3Gal-substituted PSGL1/mIgG$_{2b}$ fusion protein.

Figure 2:
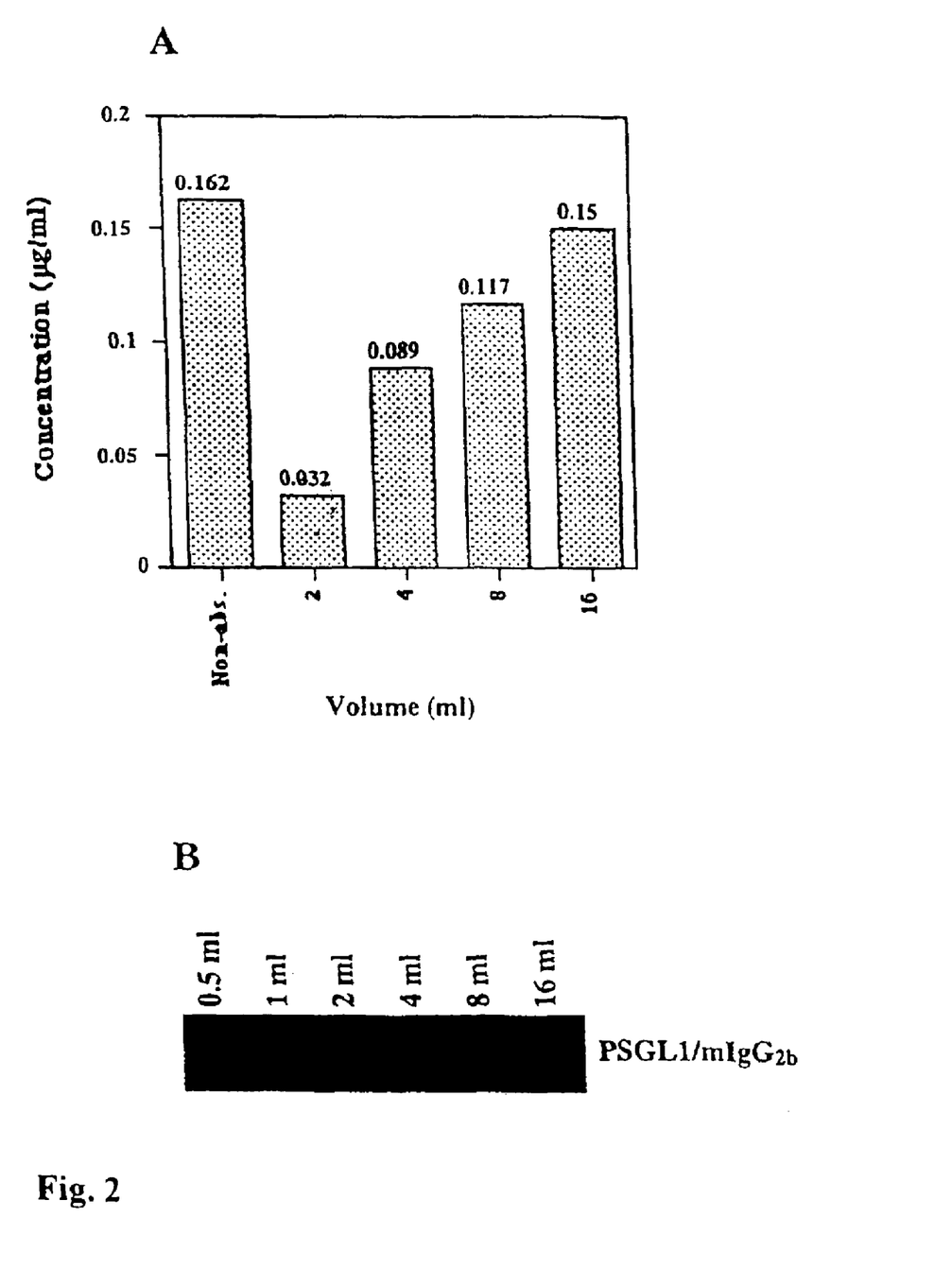
FIG. 2. Quantification by anti-mouse IgG Fc ELISA of the PSGL1/mIgG$_{2b}$ fusion protein concentration in increasing volumes of transfected COS cell supernatants before and after absorption on 50 µl of anti-mouse IgG agarose beads. Triplicate samples were analyzed.

Quantification of PSGL1/mIgG$_{2b}$ chimeras in supernatants of transfected COS cells, and on goat anti-mouse IgG agarose beads following absorption. A sandwich ELISA was employed to quantify the amount of PSGL1/mIgG$_{2b}$ in the supernatants of transfected COS cells. Typically, 5 culture flasks (260 ml flasks, Nunclon™) with COS cells at 70% confluence were transfected and incubated as described in materials and methods. Following an incubation period of 7 days in 10 ml of AIM V medium per flask, the medium was collected. The concentration of fusion protein in the supernatant from such a transfection, as well as in different volumes of supernatant following absorption on 100 µl gel slurry of anti-mouse IgG agarose beads (corresponding to 50 µl packed beads) was determined by an ELISA calibrated with purified mouse IgG Fc fragments (FIG. 2). The concentration of PSGL1/mIgG$_{2b}$ in the supernatants ranged from 150 to 200 ng/µl, and in this particular experiment it was approximately 160 ng/µl (FIG. 2 A, the non-absorbed column). The concentration of PSGL1/mIgG$_{2b}$ remaining in 2, 4 and 8 ml of supernatant following absorption on 50 µl packed anti-mouse IgG agarose beads was 32, 89 and 117 ng/µl, respectively. This corresponds to 260, 290 and 360 ng of PSGL1/mIgG$_{2b}$ being absorbed onto 50 µl packed anti-mouse IgG agarose beads from 2, 4 and 8 ml of supernatant, respectively. Western blot analysis with the *B. simplicifolia* IB$_4$ lectin revealed that 50 µl of packed beads could absorb out the PSGL1/mIgG$_{2b}$ fusion protein from 1 ml supernatant to below detectability and from 2 ml to barely detectable levels (not shown).

Figure 3:
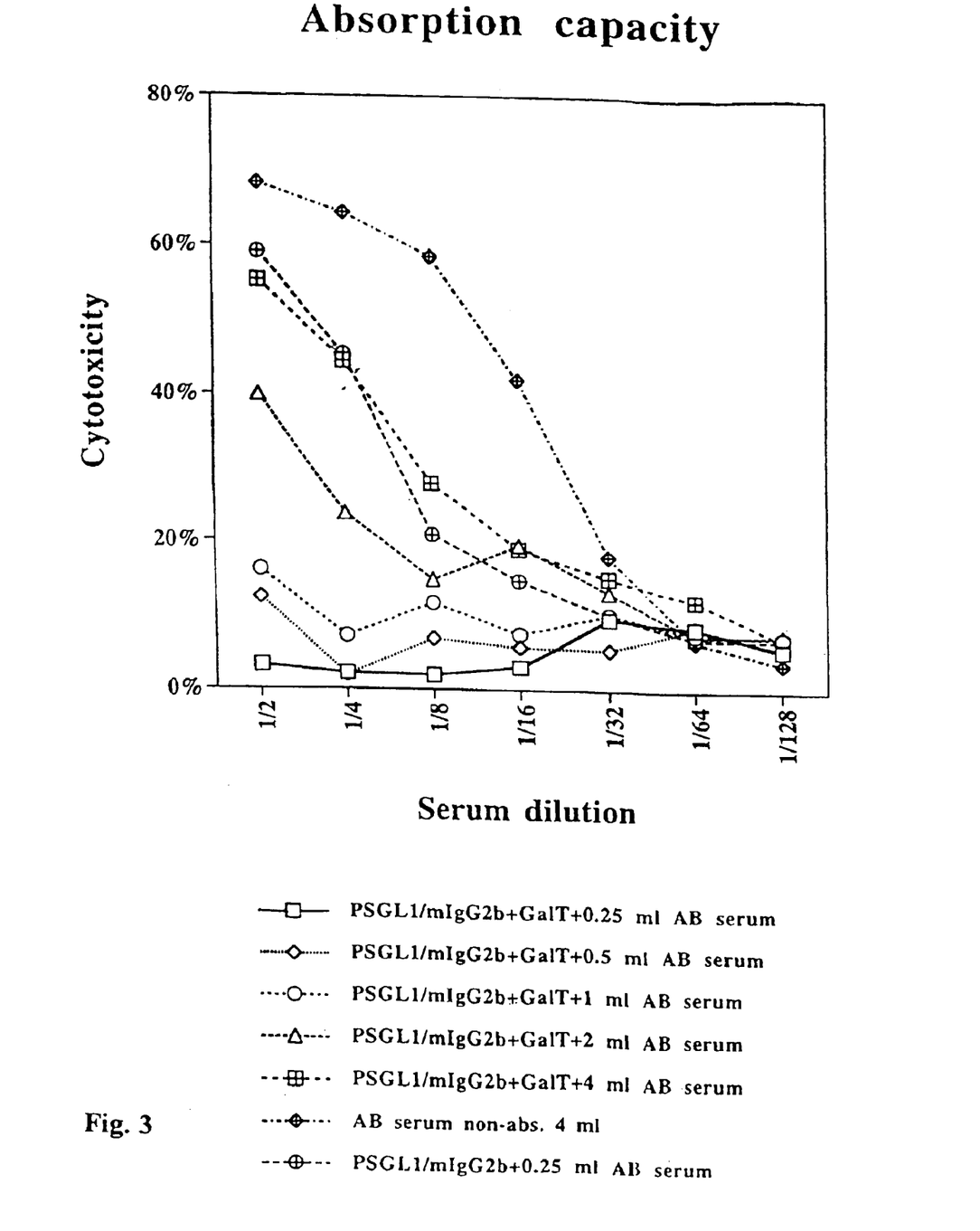
FIG. 3. Antibody-dependent, complement-mediated PEC-A cell cytotoxicity by different volumes of human AB serum following absorption on 50 µl of anti-mouse IgG agarose beads carrying approximately 300 ng of Galα1, 3Gal- or non-substituted PSGL1/mIgG$_{2b}$ as estimated in a $^{51}$Cr-release assay.

The absorption capacity of immobilized, Galα1,3Gal-substituted PSGL1/mIgG$_{2b}$. Twenty ml of supernatant from COS cells transfected with the PSGL1/mIgG$_{2b}$ plasmid alone or together with the porcine α1,3GT cDNA, were mixed with 500 µl gel slurry of anti-mouse IgG agarose beads each. Following extensive washing the beads were aliquoted such that 100 µl of gel slurry (50 µl packed beads) were mixed with 0.25, 0.5, 1.0, 2.0 and 4.0 ml of pooled, complement-depleted, human AB serum, and rolled head over tail at 4° C. for 4 hrs. Following absorption on PSGL1/mIgG$_{2b}$ and Galα1,3Gal-substituted PSGL1/mIgG$_{2b}$, the serum was assayed for porcine endothelial cell cytotoxicity in the presence of rabbit complement using a 4 hr $^{51}$Cr release assay (FIG. 3). As shown in FIG. 3, 100 µl of beads carrying approximately 300 ng of PSGL1/mIgG$_{2b}$ (see above) can reduce the cytotoxicity of 4 and 2 ml AB serum in each dilution step, and completely absorb the cytotoxicity present in 1 ml and less of human AB serum. Note that the same amount of non-Galα1,3Gal-substituted PSGL1/mIgG$_{2b}$ reduces the cytotoxicity of 0.25 ml absorbed human AB serum only slightly (FIG. 3).

Figure 4:
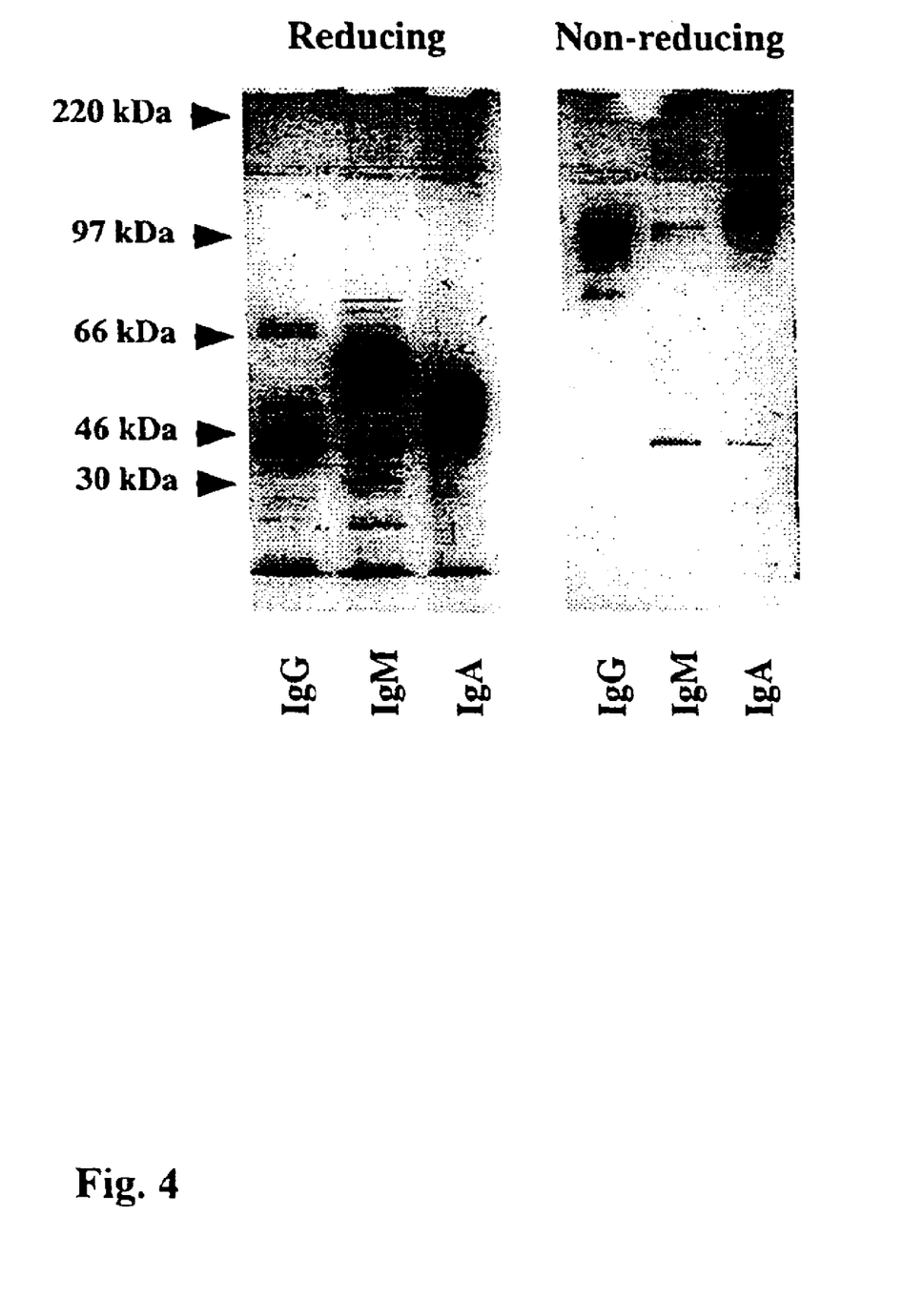
FIG. 4. Ten percent SDS-PAGE of immunoaffinity purified human IgG, IgM, and IgA. Four micrograms of each sample were run under reducing and non-reducing conditions, and proteins were visualized by silver staining. The gel migration length of molecular weight proteins of 220, 97, 66, 46 and 30 kDa is indicated on the left handside.
Figure 5:
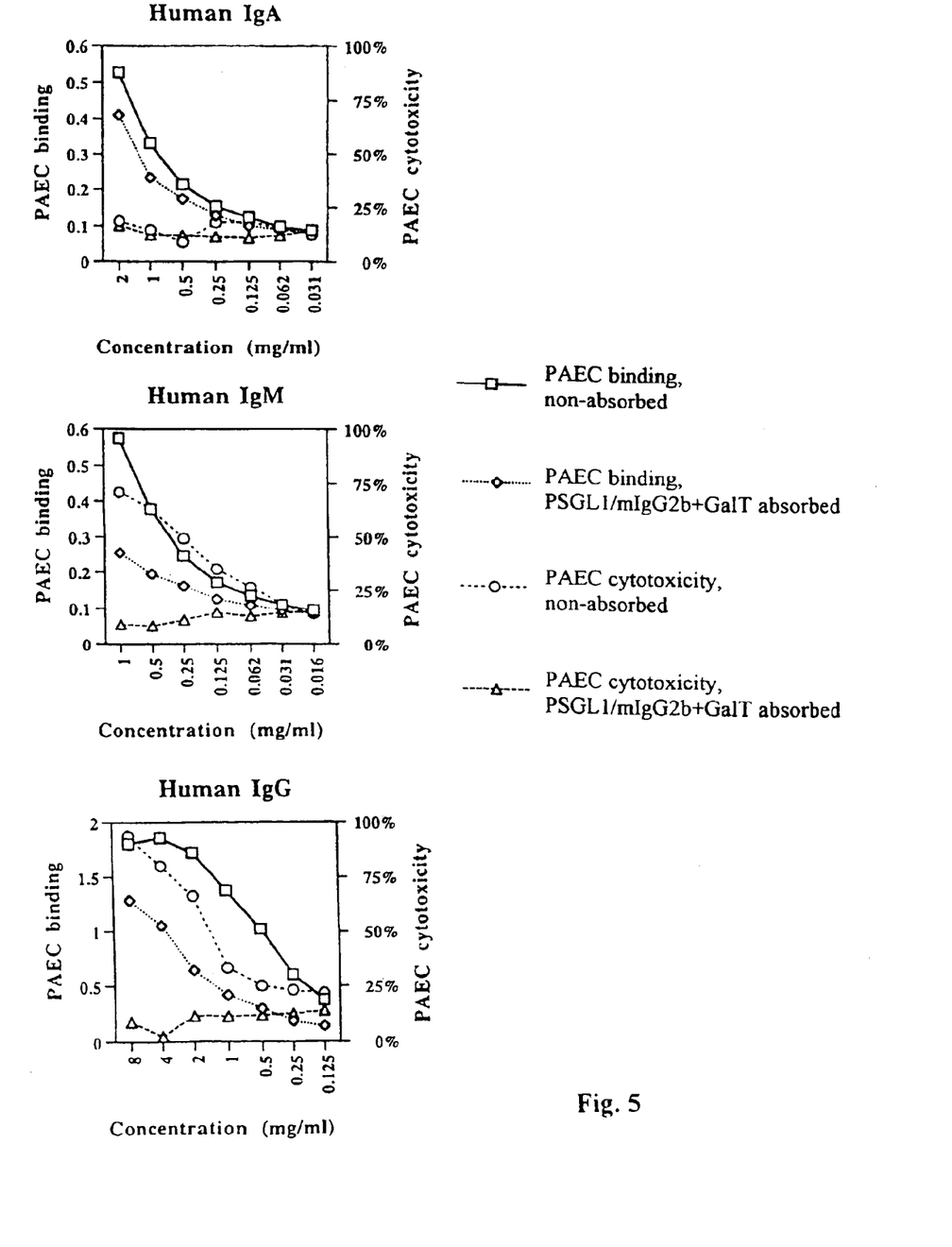
FIG. 5. The antibody-dependent, complement-mediated PEC-A cell cytotoxicity of immunoaffinity purified human IgG, IgM and IgA before and after absorption on Galα1, 3Gal-substituted PSGL1/mIgG$_{2b}$ was investigated by $^{51}$Cr-release assays (right handside Y-axis; % killing). The PEC-A cell binding of immunoaffinity purified IgG, IgM and IgA before and after absorption on Galα1,3Gal-substituted PSGL1/mIgG$_{2b}$ was estimated in a cell ELISA (left handside Y-axis; O.D. at 405 nm). The two assays were run in parallel on absorbed and non-absorbed Ig fractions. The concentration of the different Ig classes were chosen to be approximately half maximum of what is normally found in human serum.

The effect of Galα1,3Gal-substituted PSGL1/mIgG$_{2b}$ on complement-dependent porcine endothelial cell cytotoxicity and binding. To investigate the efficiency with which PSGL1/mIgG$_{2b}$ could absorb individual human immunoglobulin classes, human IgG, IgM and IgA were purified from human AB serum by immuno-affinity chromatography on anti-human IgG, IgM and IgA agarose beads. Following its isolation IgA was passed through anti-IgG and IgM columns to remove traces of IgG and IgM. This procedure was performed for the other Ig classes as well. Ig fraction purity was checked by SDS-PAGE (FIG. 4). In concentrations found in normal serum, human IgG and IgM, but not IgA, were cytotoxic for PEC-A in the presence of rabbit complement (FIG. 5). The cytotoxicity residing in the IgG and IgM fractions was completely removed by absorption on Galα1, 3Gal-substituted PSGL1/mIgG$_{2b}$. To investigate whether the lack of cytotoxicity exhibited by the IgA fraction was due to a lack of binding of human IgA antibodies to PEC-A, a cell ELISA was run with the same Ig fractions that was used in the cytotoxicity assay in order to detect bound IgG, IgM and IgA. Alkaline phosphatase-conjugated, class specific F(ab)'$_2$ fragments were used as secondary antibodies. Eventhough the cytotoxicity of IgG and IgM was completely removed by absorption on Galα1,3Gal-substituted PSGL1/mIgG$_{2b}$, the binding was never reduced with more than 70% (ranging from 30 to 70%) for IgG, and never with more than 55% (ranging from 10 to 55%) for IgM (FIG. 5). Human IgA clearly bound to PEC-A, and the binding was only slightly reduced (not more than 29%) following absorption on Galα1,3Gal-substituted PSGL1/mIgG$_{2b}$. The lack of cytotoxicity of the IgA fraction could therefore not be explained by an inability of the IgA fraction to bind PEC-A, but may be due to an inability to activate complement.

The effect of Galα1,3Gal-substituted PSGL1/mIgG$_{2b}$ on ADCC of porcine endothelial cells. Several assays have been performed under serum-free conditions where PEC-A have had an intermediate sensitivity to direct killing by freshly isolated PBMC when compared to K562 and Raji cells; K562 being sensitive and Raji non-sensitive to killing by human NK cells (FIG. 6A). In the presence of 10% human, complement-inactivated AB serum, the killing rate was almost doubled supporting an ADCC effect in vitro (FIG. 6B) in agreement with previously published data (30). However, if the serum is absorbed with the Galα1,3Gal-substituted PSGL1/mIgG$_{2b}$ under conditions known to remove all PEC-A cytotoxic antibodies (se above), the killing rate decreases to levels slightly lower than those seen under serum-free conditions. On the other hand, the PSGL1/mIgG$_{2b}$ fusion protein itself without Galα1,3Gal epitopes could not absorb out what caused the increased killing rate in the presence of human AB serum (FIG. 6B). These data support the notion that anti-pig antibodies with Galα1,3Gal specificity can support an antibody-dependent cell-mediated cytotoxicity in vitro, and that the Galα1,3Gal-substituted PSGL1/mIgG$_{2b}$ fusion protein can effectively remove these antibodies just as it effectively removes the complement-fixing cytotoxic anti-pig antibodies.

DESCRIPTION OF THE DRAWINGS

FIG. 1. Six percent SDS-PAGE of proteins isolated from supernatants of COS cells transfected with vector alone (CDM8), PSGL1/mIgG$_{2b}$, or PSGL1/mIgG$_{2b}$ and porcine α1,3GT expression plasmids. Anti-mouse IgG agarose beads were used for immunoaffinity purification of fusion proteins. Following extensive washing, the beads were boiled in sample buffer under reducing and non-reducing conditions to release absorbed proteins. Gels run in parallel were either silver stained, or used for electrophoretic transfer of separated proteins onto nitrocellulose membranes. These were subsequently probed with peroxidase-conjugated *Bandeireia simplicifolia* isolectin B$_4$ lectin and visualized by chemiluminescens to detect Galα1,3Gal epitopes on immunopurified proteins. The gel migration length of molecular weight proteins of 220, 97 and 66 kDa is indicated on the left handside.

DISCUSSION

Three major avenues of research have been followed in order to develop strategies to prevent HAR. Methods (i) to remove or neutralize anti-pig antibodies, (ii) to interfere with complement activation, and (iii) to remove or modify Galα1, 3Gal determinants, have been tested in assays in vitro, in ex vivo organ perfusions and in pig to primate transplantations.

Pretransplant pig organ perfusion (46), plasmapheresis (13, 14, 20), immunoabsorption (13, 14, 17), and absorption on synthetically made Galα1,3Gal-containing oligosaccharides coupled to a solid phase (22) have been used to remove anti-pig antibodies. Recently, oligosaccharides derived from pig gastric mucin were shown to efficiently remove anti-Galα1,3Gal-specific antibodies and thereby anti-pig cytotoxicity (24). Injection of free saccharides to block anti-pig antibodies in the circulation is an alternative route used to prevent HAR. Intravenous carbohydrate therapy was used successfully in an ABO incompatible, heterotopic cardiac allograft model in the baboon (47) and in neonates with ABO hemolytic disease (48). No deleterious effects were noticed in recipient baboons upon injection of free blood group trisaccharides at rates corresponding to 500 mg/hr following a bolus injection of 4 g of the trisaccharide (47). Free Galα1,3Gal-containing saccharides have been used in vitro to neutralize anti-pig antibodies (23), but synthetic Galα1,3Gal-containing oligosaccharides in sufficient quantities for use in pig to primate xenotransplantation models are not yet available. However, high concentrations of melibiose (Galα1,6Glc) or arabinogalactan, a naturally occurring plant polysaccharide containing non-reducing α-D-galactose, have been used to prevent the toxic effect of baboon serum on porcine PK15 cells in vitro and to prolong pig cardiac xenograft survival in transplanted baboons (49). Lethal toxic effects of the carbohydrate were observed in this study (49). Peptides mimicking the Galα1,3Gal structure (50, 51) and murine monoclonal anti-idiotypic antibodies directed against common idiotopes on naturally occurring human anti-pig antibodies (52), are new reagents that may be used to absorb or block anti-pig antibodies. In addition, anti-μ chain antibodies have been used in a guinea pig to rat xenotransplantation model to deplete xenoreactive IgM antibodies in vivo (15, 16)—a strategy that warrants further investigation in the pig to primate combination.

Cobra venom factor (20) and soluble complement receptor type 1 (21) have been used to perturb complement activation and thereby to prolong xenograft survival in pig to non-human primate transplantations. Transgenic pigs have been made in which cDNAs encoding human sequences of the species-restricted complement-regulatory proteins, CD55 and CD59, are expressed in porcine endothelium (53–55). Organs from transgenic pigs have been shown to be less prone to HAR following organ perfusion with human blood or transplantation into non-human primates (56–59).

The most recent approach to prevent HAR involves modulating the expression of Galα1,3Gal epitopes on porcine endothelium. Sandrin and McKenzie suggested and proved that the expression of a glycosyltransferase, such as an α1,2 FT, competing with the endogenous α1,3 galactosyltransferase for the same precursor carbohydrate prevented expression of Galα1,3Gal epitopes upon transfection into porcine LLC-PK1 cells (26). As a result these cells became less sensitive to antibody-mediated, complement-dependent lysis (26). Recently, two independent groups have reported the making of transgenic pigs expressing this blood group H α1,2 FT, but no data have been reported on the sensitivity of the endothelium derived from these pigs to antibody-mediated cytotoxicity (27, 28).

We describe the construction and production of a novel, efficient absorber that can be produced cheaply, in large quantities, and which can be easily coupled to a solid phase facilitating extracorporeal immunoabsorption of human blood to remove anti-pig antibodies before pig organ xenografting. To make possible the production of a highly glycosylated, recombinant protein carrying large amounts of Galα1,3Gal epitopes (FIG. 1), we made a chimeric protein by fusing the cDNA encoding the extracellular part of a membrane-anchored mucin, PSGL-1 (40), with the Fc part of mouse IgG, and coexpressed this with porcine α1,3 GT. Mucins are the main constituents of mucus, which is the gel covering all mucous membranes. The physical characteristics of mucins are due to their high content of O-linked carbohydrates (usually more than 60% of the MW). Several cell membrane-anchored proteins containing mucin-type domains have been characterized: CD34, CD43, GlyCAM-1, PSGL-1, MAdCAM, CD96, CD45, and RBC glycophorins among others (43, 44). This group of proteins has received a lot of attention since many of them have been shown to carry the carbohydrate ligands of the selectin family of adhesion molecules; CD34, MAdCAM and GlyCAM-1 carry the carbohydrate epitope recognized by L-selectin and PSGL-1 carries epitopes recognized by both E- and P-selectin (60). Two reasons made us choose the PSGL-1 extracellular part as a fusion partner. First, it has one of the longest mucin-domains known in this family of proteins and may therefore be expected to carry most O-linked carbohydrates (44, 60). Second, PSGL-1 is not only a functional ligand for E-selectin, but is the hitherto only identified protein scaffold known to present siatyl-Le$^x$ to P-selectin (61). So, if one were to make a fusion protein expressing sialyl-Le$^x$ in order to inhibit P- and E-selectin-mediated adhesion, this should contain the PSGL-1 extracellular part. We are currently investigating the possibility of making a fusion protein expressing both Galα1,3Gal and sialyl-Le$^x$ thereby exhibiting the characteristics of a dual inhibitor; one part neutralizing anti-pig antibodies and the other preventing E- and P-select-independent rolling which may be a prerequisite for leukocyte extravasation in xenograft rejection.

In a xenotransplantation situation, where pig organs for transplantation would be readily available, the recipient could be prepared by extracorporeal immunoabsorption to remove anti-pig antibodies thereby preventing HAR. Alternative strategies could be chosen (se above), but a specific removal of anti-pig antibodies would leave the patient in a more favourable state with regard to the humoral immunity as compared to plasmapheresis and protein A absorption. Therefore, immunoabsorption media containing the epitopes recognized by the anti-pig antibodies themselves would be ideal. The production of Gal$\alpha$1,31 Gal-containing di- and trisaccharides is laborious and costly, although a combination of organic and enzymatic synthesis have simplified the procedure and made it more cheap (34). Furthermore, it is not unlikely to expect the specificity of the human anti-pig antibody repertoire to be broader than just the Gal$\alpha$3Gal$\beta$4GlcNAc epitope; i.e. recognition may be modulated by the core saccharide chain, neighbouring branching points and monosaccharides, as well as modifications such as sulfation. In this context it would be better to use a glycosylated, recombinant glycoprotein modified through the action of the porcine $\alpha$1,3 GT itself resulting in a more natural array of Gal$\alpha$1,3Gal-containing structures. Three hundred ng of our fusion protein could completely remove the pig endothelial cell cytotoxic antibodies from 1 ml of human AB serum (FIG. 3), which should be compared to other studies where 1 g of oligosaccharide linked to a solid-phase was used to absorb 3 ml of human AB serum (23). However, direct comparisons are needed to state a difference in absorption capability. The fusion protein is most likely efficient due to a polyvalent expression of Gal$\alpha$1,3Gal-containing determinants and a possible expression of the epitope in a variety of structural contexts facilitating the absorption of a broader spectrum of the human anti-pig repertoire. Recent, studies with pig gastric mucin-derived oligosaccharides indicate that polyvalency is important for absorption effectiveness (24).

Human IgG, IgM and IgA were purified from pooled human AB serum (FIG. 4) in order to investigate their binding to, and cytotoxicity for, porcine aortic endothelial cells, and to evaluate the Ig class-specific absorption efficacy of the fusion protein (FIG. 5). The PAEC cytotoxicity of human IgG at 8 mg/ml and IgM at 1 mg/ml was completely removed by Gal$\alpha$1,3Gal-substituted PSGL1/mIgG$_{2b}$. However, the binding was not completely abolished as estimated in a PAEC ELISA using aliquots of the same antibody preparations as in the cytotoxicity assay. Whether this represents residual IgG and IgM binding to epitopes other than Gal$\alpha$1,3Gal on PAEC—epitopes which are not able to induce an antibody-mediated cytotoxic effect, Fc receptor binding, or just a non-specific, non-functional binding, is not known at present. In our hands, purified IgA was not cytotoxic to PAEC although it clearly bound these cells (FIG. 5). This is in contrast with a previous study by Schaapherder et al, who demonstrated cytotoxicity by dimeric human IgA via the alternative pathway of complement activation (62). However, they used serum from human agammaglobulinemic donors as complement source, whereas we used rabbit serum (62). Furthermore, we saw no clear evidence of dimeric IgA in our IgA preparations (FIG. 4). In any case, IgA clearly binds PAEC and may be involved in pig xenograft rejection through other effector mechanisms mediated by, for instance, Fc receptor binding on macrophages and neutrophils (63, 64). This emphasizes the importance of using absorbers that remove all anti-pig Ig classes, something which protein A and anti-$\mu$ chain antibody absorptions do not.

Figure 6:
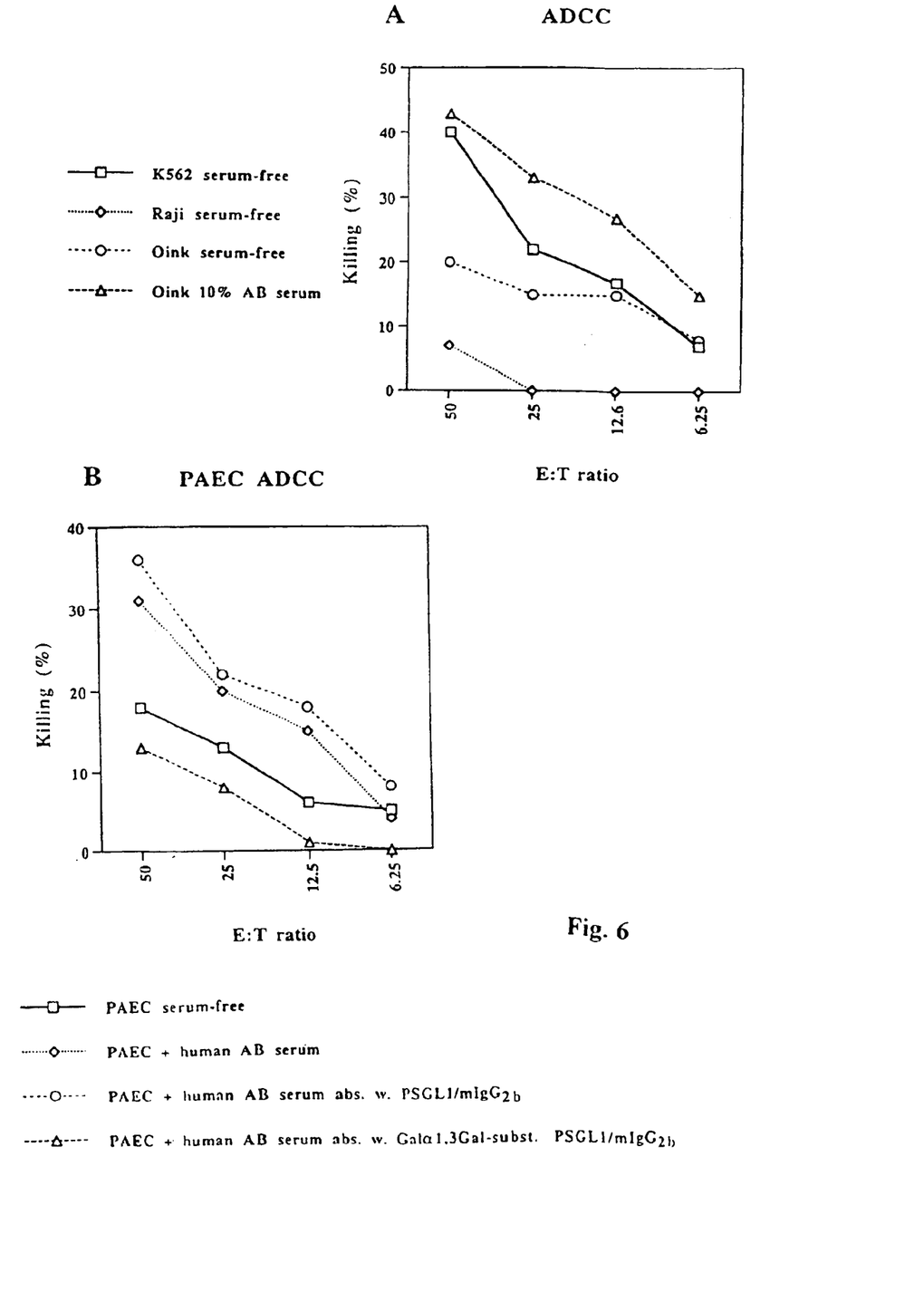
FIG. 6. The direct cytotoxic effect (serum-free conditions) of human PBMC on K562, Raji and PEC-A cells, and the potentiating effect on killing by the addition of heat-inactivated, human AB serum, was investigated in a 4 hr $^{51}$Cr-release assay (graph A). The effect of heat-inactivated, human AB serum on antibody-dependent cellular cytotoxicity of PEC-A cells was studied in a 4 hr $^{51}$Cr-release assay before and after absorption on Galα1,3Gal- and non-substituted PSGL1/mIgG$_{2b}$, respectively (graph B).

Although anti-pig antibodies to a large extent rely on complement activation for full cytotoxic effect, there are additional effector mechanisms involving antibodies that may cause pig endothelial cell cytotoxicity. Antibody-dependent cellular cytotoxicity is such a mechanism where anti-pig antibodies with Gal$\alpha$1,3Gal specificity are important for cytotoxicity even in the absence of complement (30). Therefore, we examined how absorbed and non-absorbed human AB serum contributed to PAEC cytotoxicity by human PBMC (FIG. 6). As shown in FIG. 6 human complement-depleted AB serum increased PEC-A cytotoxicity close to more than 10% in 3 out of 4 effector to target ratios. This increased cytotoxicity contributed by human AB serum was completely removed by absorption on Gal$\alpha$1,3Gal-substituted PSGL1/mIgG$_{2b}$, whereas absorbtion on PSGL1/mIgG$_{2b}$ without Gal$\alpha$1,3Gal had no effect. This clearly demonstrates that Gal$\alpha$1,3Gal-specific antibodies not only contribute to ADCC against porcine endothelial cells, but are responsible for all of the enhanced cytotoxic effect seen upon addition of human AB serum to a human PBMC/PAEC mixed culture. If this ADCC effect is present also in vivo, strategies aiming at inhibiting complement activation may not be sufficient to prevent acute pig xenograft rejection.

We have presented the construction and production of a new and effective Gal$\alpha$1,3Gal-substituted, mucin domain-containing absorber that can be used in a pretransplant extracorporeal immunoabsorption setting to remove anti-pig antibodies involved in antibody-dependent, complement- as well as cell-mediated cytotoxicity of pig endothelial cells. By stably transfecting cells to express the PSGL1/mIgG$_{2b}$ and porcine $\alpha$1,3GT cDNAs, large amounts of fusion protein can be produced at low costs for testing in pig to primate xenotransplantation models.

REFERENCES

1. Dorling A, Lechler R I. Prospects for xenografting. Curr. Opin. Immunol. 1994; 6 (5): 765–9.
2. Ye Y, Niekrasz M, Kosanke S, et al. The pig as a potential organ donor for man. A study of potentially transferable disease from donor pig to recipient man. Transplantation 1994; 57 (5): 694–703.
3. Michaels M G, Simmons R L. Xenotransplant-associated zoonoses. Strategies for prevention. Transplantation 1994; 57 (1): 1–7.
4. Caine R Y. Organ transplantation between widely disparate species. Transplant. Proc. 1970; 2 (4): 550–6.
5. Bach F H, Robson S C, Ferran C, et al. Endothelial cell activation and thromboregulation during xerograft rejection. Immunol. Rev. 1994; 141: 5–30.
6. Magee J C, Platt J L. Xenograft rejection—molecular mechanisms and therapeutic implications. Therap. Immunol. 1994; 1 (1): 45–58.
7. Platt J L, Lindman B J, Chen H, Spitalnik S L, Bach F H. Endothelial cell antigens recognized by xenoreactive human natural antibodies. Transplantation 1990; 50 (5): 817–22.
8. Good A H, Cooper D K., Malcolm A J, et al. Identification of carbohydrate structures that bind human antiporcine antibodies: implications for discordant xenografting in humans. Transplant. Proc. 1992; 24 (2): 559–62.
9. Holgersson J, Cairns T D, Karlsson E C, et al. Carbohydrate specificity of human immunoglobulin-M antibodies with pig lymphocytotoxic activity. Transplant. Proc. 1992; 24 (2): 605–8.

10. Oriol R, Ye Y, Koren E, Cooper D K. Carbohydrate antigens of pig tissues reacting with human natural antibodies as potential targets for hyperacute vascular rejection in pig-to-man organ xenotransplantation. Transplantation 1993; 56 (6): 1433–42.
11. Galili U. Interaction of the natural anti-Gal antibody with alphagalactosyl epitopes: a major obstacle for xenotransplantation in humans. Immunol. Today 1993; 14 (10): 480–2.
12. Sandrin M S, Vaughan H A, Dabkowski P L, McKenzie I F. Anti-pig IgM antibodies in human serum react predominantly with Gal(alpha 1–3)Gal epitopes. Proc. Natl. Acad. Sci. U.S.A. 1993; 90 (23): 11391–5.
13. Cairns T D, Taube D H, Stevens N, Binns R, Welsh K I. Xenografts—future prospects for clinical transplantation. Immunol. Lett. 1991; 29 (1–2): 167–70.
14. Rydberg L, Hallberg E, Björck S, et al. Studies on the removal of anti-pig xenoantibodies in the human by plasmapheresis/immunoadsorption. Xenotransplantation 1995; 2: 253–263.
15. Soares M P, Latinne D, Elsen M, Figueroa J, Bach F H, Bazin H. In vivo depletion of xenoreactive natural antibodies with an anti-mu monoclonal antibody. Transplantation 1993; 56 (6): 1427–33.
16. Soares M, Lu X, Havaux X, et al. In vivo IgM depletion by anti-mu monoclonal antibody therapy. The role of IgM in hyperacute vascular rejection of discordant xenografts. Transplantation 1994; 57 (7): 1003–9.
17. Leventhal J R, John R, Fryer J P, et al. Removal of baboon and human antiporcine IgG and IgM natural antibodies by immunoadsorption. Results of in vitro and in vivo studies. Transplantation 1995; 59 (2): 294–300.
18. Geller R L, Bach F H, Turman M A, Casali P, Platt J L. Evidence that polyreactive antibodies are deposited in rejected discordant xenografts. Transplantation 1993; 55 (1): 168–72.
19. Koren E, Milotic F, Neethling F A, et al. Murine monoclonal anti-idiotypic antibodies directed against human anti-alpha Gal antibodies prevent rejection of pig cells in culture: implications for pig-to-human organ xenotransplantation. Transplant. Proc. 1996; 28 (2): 559.
20. Leventhal J R, Sakiyalak P, Witson J, et al. The synergistic effect of combined antibody and complement depletion on discordant cardiac xenograft survival in nonhuman primates. Transplantation 1994; 57: 974–978.
21. Pruitt S K, Kirk A D, Bollinger R R, et al. The effect of soluble complement receptor type 1 on hyperacute rejection of porcine xenografts. Transplantation 1994; 57 (3): 363–70.
22. Neethling F A, Koren E, Oriol R, et al. Immunoadsorption of natural antibodies from human serum by affinity chromatography using specific carbohydrates protects pig cells from cytotoxic destruction. Transplant. Proc. 1994; 26 (3): 1378.
23. Neethling F A, Koren E, Ye Y, et al. Protection of pig kidney (PK 15) cells from the cytotoxic effect of anti-pig antibodies by alpha-galactosyl oligosaccharides. Transplantation 1994; 57 (6): 959–63.
24. Li S, Yeh J-C, Cooper D K C, Cummings R D. Inhibition of human anti-αGal IgG by oligosaccharides derived from porcine stomach mucin. Xenotransplantation 1995; 2: 279–288.
25. Cooper D K, Good A H, Ye Y, et al. Specific intravenous carbohydrate therapy: a new approach to the inhibition of antibody-mediated rejection following ABO-incompatible allografting and discordant xenografting. Transplant. Proc. 1993; 25 (1 Pt 1): 377–8.
26. Sandrin M S, Fodor W L, Mouhtouris E, et al. Enzymatic remodelling of the carbohydrate surface of a xenogenic cell substantially reduces human antibody binding and complement-mediated cytolysis. Nature Med. 1995; 1 (12): 1261–7.
27. Sharma A, Okabe J, Birch P, et al. Reduction in the level of Gal(alpha1,3)Gal in transgenic mice and pigs by the expression of an alpha(1,2)fucosyltransferase. Proc. Natl. Acad. Sci. U.S.A. 1996; 93 (14): 7190–5.
28. Koike C, Kannagi R, Takuma Y, et al. Introduction of α(1,2)-fucosyltransferase and its effect on α-Gal epitopes in transgenic pig. Xenotransplantation 1996; 3: 81–86.
29. Blakely M L, Van der Werf W J, Berndt M C, Dalmasso A P, Bach F H, Hancock W W. Activation of intragraft endothelial and mononuclear cells during discordant xenograft rejection. Transplantation 1994; 58 (10): 1059–66.
30. Seebach J D, Yamada K, McMorrom, I M, Sachs D H, DerSimonian H D. Xenogeneic human anti-pig cytotoxicity mediated by activated natural killer cells. Xenotransplantation 1996; 3: 188–197.
31. Chou D K, Dodd J, Jessell T M, Costello C E, Jungalwala F B. Identification of alpha-galactose (alpha-fucose)-asialo-GM1 glycolipid expressed by subsets of rat dorsal root ganglion neurons. J. Biol. Chem. 1989; 264 (6): 3409–15.
32. Fujiwara S, Shinkai H, Deutzmann R, Paulsson M, Timpl R. Structure and distribution of N-linked oligosaccharide chains on various domains of mouse tumour laminin. Biochem. J. 1988; 252 (2): 453–61.
33. Dasgupta S, Hogan E L, Glushka J, van Halbeek H. Branched monosialo gangliosides of the lacto-series isolated from bovine erythrocytes: characterization of a novel ganglioside, NeuGc-isooctaosylceramide. Arch. Biochem. Biophys. 1994; 310 (2): 373–84.
34. Wong C H. Enzymatic and Chemo-Enzymatic Synthesis Of Carbohydrates. Pure Appl. Chem. 1995; 67 (10): 1609–1616.
35. Seed B. An LFA-3 cDNA encodes a phospholipid-linked membrane protein homologous to its receptor CD2. Nature 1987; 329 (6142): 840–2.
36. Khodadoust M M, Candal F J, Maher S E, et al. PEC-A: An immortalized porcine aortic endothelial cell. Xenotransplantation 1995; 2: 79–87.
37. Dabkowski P L, Vaughan H A, McKenzie I F, Sandrin M S. Characterisation of a cDNA clone encoding the pig alpha 1,3 galactosyltransferase: implications for xenotransplantation. Transplant. Proc. 1993; 25 (5): 2921.
38. Dabkowski P L, Vaughan H A, McKenzie I F, Sandrin M S. Isolation of a CDNA clone encoding the pig alpha 1,3 galactosyltransferase. Transplant. Proc. 1994; 26 (3): 1335.
39. Gustafsson K, Strahan K, Preece A. Alpha 1,3 galactosyltransferase: a target for in vivo genetic manipulation in xenotransplantation. Immunol. Rev. 1994; 141: 59–70.
40. Sako D, Chang X J, Barone K M, et al. Expression cloning of a functional glycoprotein ligand for P-selectin. Cell 1993; 75 (6): 1179–86.
41. Laemmli U K. Cleavage of structural proteins during the assembly of the head of bacteriophage T4. Nature 1970; 227 (259): 680–5.
42. Towbin H, Staehelin T, Gordon J. Electrophoretic transfer of proteins from polyacrylamide gels to nitrocellulose sheets: procedure and some applications. Proc. Natl. Acad. Sci. U.S.A 1979; 76 (9): 4350–4.
43. Carraway K L, Hull S R. Cell surface mucin-type glycoproteins and mucin-like domains. Glycobiology 1991; 1 (2): 131–8.

44. Shimizu Y, Shaw S. Mucins in the mainstream. Nature 1993; 366: 630–631.
45. Galili U, Macher B A, Buehler J, Shohet S B. Human natural anti-α-galactosyl IgG. II. The specific recognition of α(1–3)-linked galactose residues. J. Exp. Med. 1985; 162: 573–582.
46. Platt J L, Fischel R J, Matas A J, Reif S A, Bolman R M, Bach F H. Immunopathology of hyperacute xenograft rejection in a swine-to-primate model. Transplantation 1991; 52 (2): 214–20.
47. Cooper D K, Ye Y, Niekrasz M, et al. Specific intravenous carbohydrate therapy. A new concept in inhibiting antibody-mediated rejection—experience with ABO-incompatible cardiac allografting in the baboon. Transplantation 1993; 56 (4): 769–77.
48. Romano E L, Soyano A, Linares J. Preliminary human study of synthetic trisaccharide representing blood substance A. Transplant. Proc. 1987; 19 (6): 4475–8.
49. Ye Y, Neethling F A, Niekrasz M, et al. Evidence that intravenously administered alpha-galactosyl carbohydrates reduce baboon serum cytotoxicity to pig kidney cells (PK15) and transplanted pig hearts. Transplantation 1994; 58 (3): 330–7.
50. Vaughan H A, Oldenburg K R, Gallop M A, Atkin J D, McKenzie I F C, Sandrin M S. Recognition of an octapeptide sequence by multiple Galα(1,3)Gal-binding proteins. Xenotransplantation 1996; 3: 18–23.
51. Kooyman D L, McClellan S B, Parker W, et al. Identification and characterization of a galactosyl peptide mimetic. Implications for use in removing xeno-reactive anti-α Gal antibodies. Transplantation 1996; 61 (6): 851–5.
52. Koren E, Milotic F, Neethling F A, et al. Monoclonal antiidiotypic antibodies neutralize cytotoxic effects of anti-αGal antibodies. Transplantation 1996; 62: 837–843.
53. Fodor W L, Williams B L, Matis L A, et al. Expression of a functional human complement inhibitor in a transgenic pig as a model for the prevention of xenogeneic hyperacute organ rejection. Proc. Natl. Acad. Sci. U.S.A. 1994; 91 (23): 11153–7.
54. Rosengard A M, Cary N R, Langford G A, Tucker A W, Wallwork J, White D J. Tissue expression of human complement inhibitor, decay-accelerating factor, in transgenic pigs. A potential approach for preventing xenograft rejection. Transplantation 1995; 59 (9): 1325–33.
55. Diamond L E, McCurry K R, Martin M J, et al. Characterization of transgenic pigs expressing functionally active human CD59 on cardiac endothelium. Transplantation 1996; 61 (8): 1241–9.
56. Kroshus T J, Bolman R M, III, Dalmasso A P, et al. Expression of human CD59 in transgenic pig organs enhances organ survival in an ex vivo xenogeneic perfusion model. Transplantation 1996; 61 (10): 1513–21.
57. Pascher A, Poehlein C H, Storck M, et al. Human decay accelerating factor expressed on endothelial cells of transgenic pigs affects complement activation in an ex vivo liver perfusion model. Transplant. Proc. 1996; 28 (2): 754–5.
58. Tolan M J, Friend P J, Cozzi E, et al. Life-supporting transgenic kidney transplants in a pig-to-primate model. XVI International congress of the transplantation society. Barcelona, 1996: 102.
59. Schmoeckel M, Nollert G, Shahmohammadi M, et al. Prevention of hyperacute rejection by human decay accelerating factor in xenogeneic perfused working hearts. Transplantation 1996; 62 (6): 729–734.
60. Rosen S D, Bertozzi C R. Leukocyte adhesion: Two selectins converge on sulphate. Curr. Biol. 1996; 6 (3): 261–264.
61. Asa D, Raycroft L, Ma L, et al. The P-Selectin Glycoprotein Ligand Functions As a Common Human Leukocyte Ligand For P- and E-Selectins. J. Biol. Chem. 1995; 270 (19): 11662–11670.
62. Schaapherder A F, Gooszen H G, te Bulte M T, Daha M R. Human complement activation via the alternative pathway on porcine endothelium initiated by IgA antibodies. Transplantation 1995; 60 (3): 287–91.
63. Gauldi J, Richards C, Lamontagne L. Fc receptors for IgA and other immunoglobulins on resident and activated alveolar macrophages. Mol. Immunol. 1983; 20: 1029–1037.
64. Monteiro R C, Kubagawa H, Cooper M. Cellular distribution, regulation, and biochemical nature of an Fcα receptor in humans. J. Exp. Med. 1990; 171: 597–613.

What is claimed is:

1. A dimerized fusion polypeptide comprising a first polypeptide operably linked to a second polypeptide, wherein the first polypeptide:
    (a) comprises a P-selectin glycoprotein ligand-1; and
    (b) is glycosylated by an α1,3 galactosyltransferase and the second polypeptide comprises an immunoglobulin Fc region.

2. The fusion polypeptide of claim 1, wherein the first polypeptide comprises multiple Galα1,3Gal epitopes.

3. The fusion polypeptide of claim 1, wherein the α1,3 galactosyltransferase is porcine.

* * * * *